US005705091A

United States Patent [19]

Steichen et al.

[11] Patent Number: 5,705,091

[45] Date of Patent: Jan. 6, 1998

[54] ALKOXYLATED PERACID ACTIVATORS

[75] Inventors: Dale S. Steichen, Danbury, Conn.; Richard J. Wiersema, Idaho Falls, Id.

[73] Assignee: The Clorox Company, Oakland, Calif.

[21] Appl. No.: 526,705

[22] Filed: Sep. 11, 1995

[51] Int. Cl.[6] .............................. C09K 3/00; C11D 3/39; C11D 1/28; C07C 59/00

[52] U.S. Cl. .............................. 252/186.38; 252/186.39; 510/312; 510/314; 558/271; 554/90; 554/95; 554/121

[58] Field of Search .............................. 252/186.38, 186.39; 510/312, 313, 314; 558/271; 554/95, 90, 121

[56] References Cited

U.S. PATENT DOCUMENTS

| | | | |
|---|---|---|---|
| 2,955,905 | 10/1960 | Davies et al. | 8/111 |
| 3,130,165 | 4/1964 | Brocklehurst | 510/312 |
| 3,256,198 | 6/1966 | Matzner | 510/378 |
| 3,272,750 | 9/1966 | Chase | 8/111 |
| 3,925,234 | 12/1975 | Hachmann et al. | 502/167 |
| 3,960,743 | 6/1976 | Nakagawa et al. | 510/376 |
| 3,996,152 | 12/1976 | Edwards et al. | 252/186.26 |
| 4,003,841 | 1/1977 | Hachmann et al. | 510/312 |
| 4,182,726 | 1/1980 | Illuminati et al. | 558/270 |
| 4,283,301 | 8/1981 | Diehl | 510/312 |
| 4,337,213 | 6/1982 | Marynowski et al. | 562/6 |
| 4,403,056 | 9/1983 | Giolito et al. | 524/280 |
| 4,412,934 | 11/1983 | Chung et al. | 252/186.38 |
| 4,483,778 | 11/1984 | Thompson et al. | 510/376 |
| 4,486,327 | 12/1984 | Murphy et al. | 510/376 |
| 4,536,314 | 8/1985 | Hardy et al. | 510/376 |
| 4,539,130 | 9/1985 | Thompson et al. | 510/376 |
| 4,585,150 | 4/1986 | Beacham et al. | 222/129 |
| 4,609,501 | 9/1986 | Mark | 558/270 |
| 4,681,592 | 7/1987 | Hardy et al. | 8/111 |
| 4,686,061 | 8/1987 | Nollet et al. | 510/312 |
| 4,735,740 | 4/1988 | Zielske | 510/312 |
| 4,778,618 | 10/1988 | Fong et al. | 252/186.23 |
| 4,957,647 | 9/1990 | Zielske | 252/186.38 |
| 4,985,180 | 1/1991 | Bellis et al. | 554/44 |
| 5,030,380 | 7/1991 | Moschner et al. | 252/186.2 |
| 5,043,089 | 8/1991 | Nollet et al. | 510/376 |
| 5,175,333 | 12/1992 | Kerschner et al. | 558/271 |
| 5,182,045 | 1/1993 | Rowland et al. | 252/186.38 |
| 5,235,077 | 8/1993 | Amini et al. | 554/152 |
| 5,364,554 | 11/1994 | Stanislowski et al. | 252/186.38 |
| 5,391,812 | 2/1995 | Rowland et al. | 252/186.38 |
| 5,403,509 | 4/1995 | Pajol et al. | 510/535 |
| 5,545,349 | 8/1996 | Kurii et al. | 252/186.38 |

FOREIGN PATENT DOCUMENTS

| | | |
|---|---|---|
| 0098129 | 2/1987 | European Pat. Off. . |
| 0426217A2 | 5/1991 | European Pat. Off. . |
| 2-132195 | 5/1990 | Japan . |
| 3-140400 | 6/1991 | Japan . |
| WO9216491 | 10/1992 | WIPO . |

OTHER PUBLICATIONS

Greene, Theodora W., Protective Groups in Organic Synthesis, New York: John Wiley & Sons, p. 183 (in Chapter 5, entitled "Protection for the Carboxyl Group"). (1973).

*Primary Examiner*—Joseph D. Anthony

*Attorney, Agent, or Firm*—Majestic, Parsons, Siebert & Hsue

[57] ABSTRACT

Bleaching compositions are provided that comprise peracid activators. The peracid activators are ester derivatives of a carboxylic acid where the oxygen is covalently bound through a polyhydroxy linking group to a leaving group that is displaceable in a peroxygen bleaching solution by perhydroxide anion. When the peracid activator is combined with a source of peroxygen in aqueous solution, then a stain removing peracid is formed. One embodiment of the peracid activator has the structure

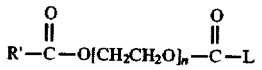

where R' is a branched or linear $C_{4-12}$ alkyl, n is 1 to about 7, and L is a leaving group.

5 Claims, No Drawings

ALKOXYLATED PERACID ACTIVATORS

TECHNICAL FIELD

This invention generally relates to peracid bleaching, and more particularly to peracid precursors or activators that are ester derivatives of carboxylic acid, have ethoxy or propoxy linking groups adjacent to a leaving group displaceable by perhydroxide anion, such as precursors having the formula

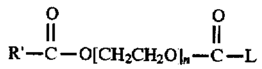

where R' is a branched or linear alkyl group, n is 1 to about 7, and L is a leaving group that is displaced in a peroxygen bleaching solution by perhydroxide anion.

BACKGROUND OF THE INVENTION

Peroxy compounds are effective bleaching agents, and compositions including mono- or di-peroxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid presents a problem of storage stability for compositions consisting of or including peroxyacids.

One approach to the problem of reduced bleaching activity of peroxyacid compositions has been to include "activators" for or precursors of peroxyacids. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester. However, these bleach activators tend to yield an unpleasant odor under actual wash conditions. U.S. Pat. No. 4,486,327, inventors Murphy et al., issued Dec. 4, 1984, and U.S. Pat. No. 4,536,314, inventors Hardy et al., issued Aug. 20, 1985, disclose certain alpha substituted derivatives of $C_6$–$C_{18}$ carboxylic acids which are said to activate peroxygen bleaches and are said to reduce malodor.

U.S. Pat. No. 4,539,130, inventors Thompson et al., issued Sep. 3, 1985 (and its related U.S. Pat. No. 4,483,778, inventors Thompson et al., issued Nov. 20, 1984) disclose chloro, methoxy or ethoxy substituted on the carbon adjacent to the acyl carbon atom. U.S. Pat. No. 3,130,165, inventor Brocklehurst, issued Apr. 21, 1964, also discloses an α-chlorinated peroxyacid, which is said to be highly reactive and unstable.

U.S. Pat. No. 4,681,952, inventors Hardy et al., issued Jul. 21, 1987, discloses peracids and peracid precursors said to be of the general type RXAOOH and RXAL, wherein R is said to be a hydrocarbyl group, X is said to be a hetero-atom, A is said to be a carbonyl bridging group, and L is a leaving group, such as an oxybenzene sulfonate. $C_6$ through $C_{20}$ alkyl substituted aryl are said to be preferred as R, with $C_6$–$C_{15}$ alkyl said to be especially preferred for oxidative stability.

Chung et al., U.S. Pat. No. 4,412,934, issued Nov. 1, 1983, discloses bleaching compositions containing a peroxygen bleaching compound and a bleach activator of the general formula

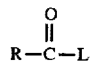

wherein R is an alkyl group containing from about 5 to about 18 carbon atoms, and L is a leaving group, the conjugate acid of which has a $pK_\alpha$ in the range of about 6 to about 13.

Nakagawa et al., U.S. Pat. No. 3,960,743, issued Jun. 1, 1976, discloses an activating agent represented by the formula

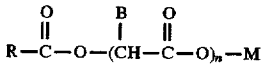

wherein R stands for an alkyl group having 1 to 15 carbon atoms, a halogen- or hydroxyl-substituted alkyl group having 1 to 16 carbon atoms or a substituted aryl group, B designates a hydrogen atom or an alkyl group having 1 to 3 carbon atoms, M represents a hydrogen atom, an alkyl group having 1 to 4 carbon atoms or an alkali metal, and n is an integer of at least 1 when M is an alkyl group or n is an integer of at least 2 when M is a hydrogen atom or an alkali metal. However, perhydrolysis of this activating agent substantially does not occur at the carbonyl adjacent the M substituent and the overall perhydrolysis that does occur tends to occur relatively slowly.

U.S. Pat. No. 4,778,618, Fong et al., issued Oct. 18, 1988, provides novel bleaching compositions comprising peracid precursors with the general structure

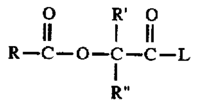

wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_{3\alpha+}$, wherein $R^\alpha$ is $C_{1-30}$ alkyl; and where L is a leaving group which can be displaced in a peroxygen bleaching solution by perhydroxide anion. U.S. Pat. Nos. 5,182,045, issued Jan. 26, 1993, and 5,391,812, issued Feb. 21, 1995, inventors Rowland et al., are similar, but are polyglycolates of the Fong et al. monoglycolate precursors, or activators.

U.S. Pat. No. 4,985,180, issued Jan. 15, 1991, inventors Bellis et al., describes the preparation of bleach activator compounds in a two-step process where a phenol derivative is reacted with an α-haloacetyl halide to yield a phenyl ester intermediate followed by reacting the intermediate with a nucleophile. Thus, for example, an intermediate such as 4-(chloroacetyloxy)benzene sulfonic acid, sodium slat, can be prepared from 4-hydroxybenzene sulfonic acid, mixed xylenes, and chloroacetyl chloride in the presence of a tetra-n-butylphosphonium chloride catalyst.

U.S. Pat. No. 5,235,077, issued Aug. 10, 1993, inventors Amini et al., describes the preparation of activators through reactions of phenyl chloroacetate with a $C_6$–$C_{12}$ carboxylic acid. This patent refers to U.S. application Ser. No. 07/674,401, for a process describing preparation of the phenylchloroacetate. Said U.S. application was published in the form of its corresponding European application, WO92/16491, published Oct. 1, 1992, inventors Dumas et al. In this publication, phenylchloroacetate is prepared by reacting chloroacetyl chloride with phenol in the presence of a catalyst.

New peracid activators that provide good bleaching remain desirable for laundry and household bleaching and cleaning applications.

SUMMARY OF THE INVENTION

A bleaching composition in accordance with the invention comprises a peracid activator being an ester derivative of a carboxylic acid including the moiety

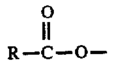

where R is $C_{1-20}$ linear or branched alkyl, alkylethoxylated, cycloalkyl, aryl, or a substituted aryl. A leaving group is covalently bound to the oxygen of said moiety through a polyhydroxy linking group, such as an ethoxy or a propoxy. The leaving group is displaceable in a peroxygen bleaching solution by perhydroxide anion. When this peracid activator is combined with a source of peroxygen in aqueous solution, then a stain removing peracid is formed.

Particularly preferred activators have the structure

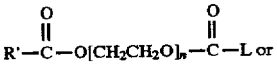 or 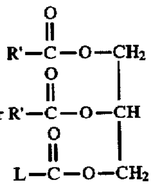

where R' is a branched or linear $C_{4-12}$ alkyl, and n is 1 to about 7.

Embodiments of the invention have shown significant bleaching on various stains, such as bandy-black clay which correlates well with "dingy-soil" cleaning on consumer garments. Because peracid activators of the invention include polyhydroxide linking groups, such as ethoxy or propoxy, the degree of ethoxylation or propoxylation can be selected to adjust the hydrophylic and hydrophobic balance of the compound.

DETAILED DESCRIPTION OF PREFERRED EMBODIMENTS

The invention provides peracid activators (sometimes also known as peracid precursors) and bleaching compositions including peracid activators. By peracid activators are meant reactive esters which have a leaving group substituent. During perhydrolysis the leaving group cleaves off at the acyl portion of the ester. By perhydrolysis is meant the reaction that occurs when a peracid activator is combined in a reaction medium (aqueous solution) with an effective amount of a source of hydrogen peroxide. The leaving group is a substituent which is attached via an oxygen bond to the acyl portion of the ester and which can be replaced by a perhydroxide anion (—OOH) during perhydrolysis.

Formulas 1A and 1B illustrate two particularly preferred peracid activator embodiments of this invention.

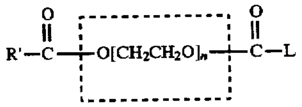

FORMULA 1A

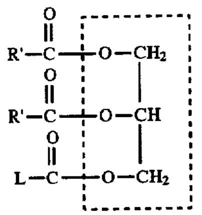

FORMULA 1B where L is a leaving group, R' is a branched or linear alkyl preferably having about 4 to about 12 carbons, and n is 1 to about 7.

As may be seen by the polyhydroxy derivative moieties within the dashed line boxes of Formulas 1A and 1B, peracid activators in accordance with this invention broadly have the structure

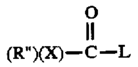

where X is a polyhydroxy derivative and R" is one or more

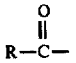

(with R being $C_{1-20}$ linear or branched alkyl, alkylethoxylated, cycloalkyl, aryl, or substituted aryl), or more preferably one or two of

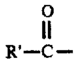

where R' is $C_{4-12}$ alkyl or alkoxylated alkyl. Branched or unbranched alkyl groups for R' are particularly desirable when the activators is used to form surface active peracids for oxidizing soils and stains affixed to fabric surfaces at relatively low wash temperatures. R' can also be monounsaturated or polyunsaturated. The polyhydroxy derivative moieties "X," illustrated by the dashed line boxes of Formulas 1A and 1B, are preferably ethoxy and propoxy (branched or unbranched) groups, which can be present per mole of ester as from 1-30 ethoxy or propoxy groups, and mixtures thereof.

Particularly preferred peracid activators of the invention provide enhanced bleaching activity and are a very stable source of peracid. Also, because peracid activators of the invention include polyhydroxy linking groups, such as ethoxy or propoxy, the degree of ethoxylation or propoxylation can be selected easily to adjust the hydrophilic and hydrophobic balance of the compounds, as desired. That is, peracid activators of the invention can be selectively ethoxylated or propoxylated by simple transesterification of a fatty acid triglyceride with ethylene or propylene glycol. Use of the ethoxylate or propoxylate also minimizes a tendency towards an unpleasant odor found with many other peroxy acids of the prior art.

The carbonyl containing moiety of the carboxylic acid ester derivative is covalently bound (via the oxygen of the carbonyl containing moiety) through a polyhydroxy linking group to the leaving group. The polyhydroxy linking group constitutes a triglyceride-like backbone. Thus, in the one embodiment illustrated by Formula 1A, the linking group is one or more ethoxys, whereas the linking group of the Formula 1B embodiment can be viewed as having a propoxy linking group (with the triglyceride like backbone). Of the two embodiments, the ethoxy linking group embodiment is the more preferred.

Compounds of the invention are readily prepared. For example, an embodiment of the Formula 1A invention was prepared by using an alkanoyl chloride (e.g. octanoyl chloride) and ethylene glycol as starting materials. These two were reacted in ethyl acetate in the presence of pyridine. The resulting hydroxy ethyl ester was isolated by distillation and then reacted with phosgene to form the chloroformate. The chloroformate in turn was reacted with monosodium phenylsulfonate in the presence of pyridine to form the sodium salt of the desired product. This was isolated by conversion to the free acid and extraction into ethyl acetate. The ethyl acetate was removed in a rotovap. The free acid was dissolved in methanol and converted to the sodium salt with sodium carbonate.

Where Formula 1B embodiments are desired, then glycerine fatty acids, sorbitan esters, sugar esters, and alkyl glycosides may be used as starting materials. Such alkyl/polyol compounds have alkyl to polyol mole ratios selected to provide desired peracid. Thus, shorter alkyls ($C_6$–$C_8$) preferably utilize polyol mole ratios of less than or about equal to 1. Longer alkyls ($C_{12}$–$C_{16}$) preferably use polyol mole ratios of about equal to or greater than 3. Such alcohol polyols (be they primary, which are preferred, or secondary) react with phosgene along the general lines as already described for the Formula 1A embodiments. One can obtain a mixture of primary and/or secondary carbonate esters, or polycarbonate esters. Illustrative glycerine fatty acids, converted to glycerine monoesters, sorbitan esters, sugar esters, and alkyl glycosides are described, for example, in "Surfactants in Consumer Products," *Theory, Technology & Applications*, Springer-Verlag (ed. Falbe, 1987).

Preferred leaving groups are phenol sulfonate derivatives (especially sodium p-phenyl sulfonate). However, other leaving groups include: other phenol derivatives, halides, oxynitrogen leaving groups, and carboxylic acid (from a mixed anhydride). Each of these leaving groups will be more specifically described hereinafter.

Phenol Derivative Leaving Groups

The phenol derivatives can be generically defined as:

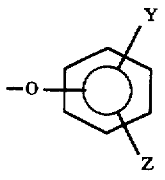

wherein Y and Z are, individually H, $SO_3M$, $CO_2M$, $SO_4M$, OH, halo substituent, —$OR^2$, $R^3$, $NR_3{}^4X$, and mixtures thereof, wherein M is an alkali metal or alkaline earth counterion, $R^2$ of the $OR^2$ substituent is $C_{1-20}$ alkyl, $R^3$ is $C_{1-6}$ alkyl, $R^4$ of the $NR_3{}^4$ substituent $C_{1-30}$ alkyl, X is one or more counterions, and Y and Z can be the same or different.

The alkali metal counterions to sulfonate, sulfate or carboxy (all of which are solubilizing groups) include $K^+$, $Li^+$ and most preferably, $Na^+$. The alkaline earth counterions include $Sr^{++}$, $Ca^{++}$, and most preferably, $Mg^{++}$. Ammonium ($NH_4{}^+$) and other positively charged counterions may also be suitable. The halo substituent can be F, Br or most preferably, Cl. When —$OR^2$, alkoxy, is the substituent on the phenyl ring, $R^2$ is $C_{1-20}$, and the criteria defined for R on the acyl group apply. When $R^3$ is the substituent on the phenyl ring, it is a $C_{1-10}$ alkyl, with preference given to methyl, ethyl, N- and isopropyl, N-, sec- and tert-butyl, which is especially preferred. When —$NR_3{}^4X$ (i.e. quaternary ammonium) is the substituent, it is preferred that two of $R^4$ be short chain alkyls ($C_{1-4}$, most preferably, methyl) and one of the $R^4$ alkyls be longer chain alkyl (e.g., $C_{8-30}$), with X, a negative counterion, preferably selected from halogen (Cl-, F-, Br-, I-), $CH_3SO_4$— (methosulfate), $NO_3$—, or OH—.

As already mentioned, especially preferred are phenol sulfonate leaving groups. A preferred synthesis of phenol sulfonate esters which could be adapted for use herein is disclosed in U.S. Pat. No. 4,735,740, inventor Alfred G. Zielske, entitled "Diperoxyacid Precursors and Method" issued Apr. 5, 1988. Thus, especially preferred phenol derivatives are:

—O—Ø—$SO_3M$ (especially sodium p-phenyl sulfonate)

—O—Ø—OH (p-, o- or m-dihydroxybenzene)

—O—Ø—$C(CH_3)_3$ (t-butyl phenol)

—O—Ø—$CO_2H$ (4-oxy-benzoic acid)

Halide Leaving Groups

The halide leaving groups are quite reactive and actually are directly obtained as the intermediates in the synthesis of the phenyl sulfonate and t-butyl-phenol esters. While halides include Br and F, Cl is most preferred.

Oxynitrogen Leaving Groups

The oxynitrogen leaving groups are suitable as leaving groups. In U.S. Pat. No. 4,957,647, entitled "Acyloxynitrogen Peracid Precursors", inventor Alfred G. Zielske, commonly assigned to The Clorox Company, incorporated herein by reference, a detailed description of the synthesis of these leaving groups is disclosed. The oxynitrogen leaving groups are generally disclosed as —$ONR^6$, wherein $R^6$ comprises at least one carbon which is singly or doubly bonded directed to N. Thus, —$ONR^6$ is more specifically defined as:

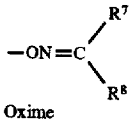

Oxime

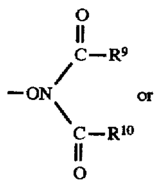

or

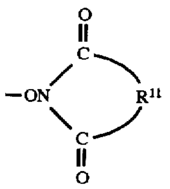

Hydroximide

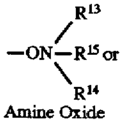

or

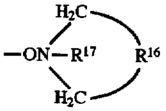

Amine Oxide

Oxime leaving groups have the structure

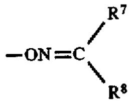

wherein $R^7$ and $R^8$ are individually H, $C_{1-20}$ alkyl, (which can be cycloalkyl, straight or branched chain), aryl, or alkylaryl and at least one of $R^7$ and $R^8$ is not H. Preferably $R^7$ and $R^8$ are the same or different, and range from $C_{1-6}$. Oximes are generally derived from the reaction of hydroxylamine with either aldehydes or ketones.

Examples of oxime leaving groups are: oximes of aldehydes (aldoximes), e.g., acetaldoxime, benzaldoxime, propionaldoxime, butylaldoxime, heptaldoxime, hexaldoxime, phenylacetaldoxime, p-tolualdoxime, anisaldoxime, caproaldoxime, valeraldoxime and p-nitrobenzaldoxime; and oximes of ketones (ketoximes), e.g., acetone oxime (2-propanone oxime), methyl ethyl ketoxime (2-butanone oxime), 2-pentanone oxime, 2-hexanone oxime, 3-hexanone oxime, cyclohexanone oxime, acetophenone oxime, benzophenone oxime and cyclopentanone oxime.

Particularly preferred oxime leaving groups are:

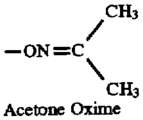

Acetone Oxime

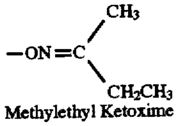

Methylethyl Ketoxime

Hydroxyimide leaving groups comprise:

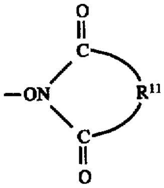 or 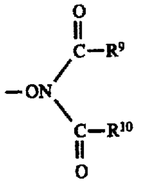

wherein $R^9$ and $R^{10}$ can be the same or different, and are preferably straight chain or branched $C_{1-20}$ alkyl, aryl, alkylaryl or mixtures thereof. If alkyl, $R^9$ and $R^{10}$ can be partially unsaturated. It is especially preferred that $R^9$ and $R^{10}$ are straight or branched chain $C_{1-6}$ alkyl, which can be the same or different. $R^{11}$ is preferably $C_{1-20}$ alkyl, aryl or alkylaryl, and completes a heterocycle. For example, a preferred structure is

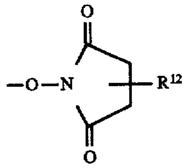

wherein $R^{12}$ can be an aromatic ring fused to the heterocycle, or $C_{1-6}$ alkyl (which itself could be substituted with water solubilizing groups, such as EO, PO, $CO_2$— and $SO_3$—).

The esters of imides can be prepared as described in Greene, *Protective Groups in Organic Synthesis*, p. 183, and are generally the reaction products of acid chlorides and hydroxymides.

Examples of N-hydroxyimides which will provide the hydroxyimide leaving groups of the invention include: N-hydroxysuccinimide, N-hydroxyphthalimide, N-hydroxyglutarimide, N-hydroxynaphthalimide, N-hydroxymaleimide, N-hydroxydiacetylimide and N-hydroxydipropionylimide.

Especially preferred examples of hydroxyimide leaving groups are:

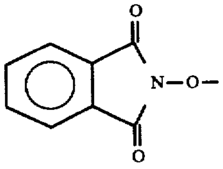

Oxysuccinimide

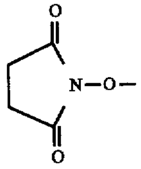

Oxyphthalimide

Amine oxide leaving groups comprise:

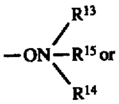 or 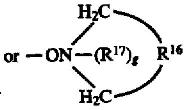

In the first preferred structure for amine oxides, $R^{13}$ and $R^{14}$ can be the same or different, and are preferably $C_{1-20}$ straight or branched chain alkyl, aryl, alkylaryl or mixtures thereof. If alkyl, the substituent could be partially unsaturated. Preferably, $R^{13}$ and $R^{14}$ are $C_{1-4}$ alkyls and can be the same or different. $R^{15}$ is preferably $C_{1-30}$ alkyl, aryl, alkylaryl and mixtures thereof. This $R^{15}$ substituent could also be partially unsaturated. It is more preferred that $R^{13}$ and $R^{14}$ are relatively short chain alkyl groups ($CH_3$ or $CH_2CH_3$) and $R^{15}$ is preferably $C_{1-20}$ alkyl, forming together a tertiary amine oxide.

Further, in the second preferred amine oxide structure, $R^{16}$ can be $C_{1-20}$ alkyl, aryl or alkylaryl, and completes a heterocycle. $R^{16}$ preferably completes an aromatic heterocycle of 5 carbon atoms and can be alkyl or aryl substituted. $R^{17}$ is preferably nothing, $C_{1-30}$ alkyl, aryl, alkylaryl or mixtures thereof, with g=0 or 1. $R^{17}$ is more preferably $C_{1-20}$ alkyl if $R^{16}$ completes an aliphatic heterocycle. If $R^{16}$ completes an aromatic heterocycle, $R^{17}$ is nothing.

Examples of amine oxides suitable for use as leaving groups herein can be derived from: pyridine N-oxide, trimethylamine N-oxide, 4-phenyl pyridine N-oxide, decyldimethylamine N-oxide, dodecyldimethylamine N-oxide, tetradecyldimethylamine N-oxide, hexadecyldimethylamine oxide, octyldimethylamine N-oxide, di(decyl)methylamine N-oxide, di(dodecyl)methylamine N-oxide, di(tetradecyl) methylamine N-oxide, 4-picoline N-oxide, 3-picoline N-oxide and 2-picoline N-oxide.

Especially preferred amine oxide leaving groups include:

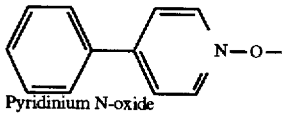

Pyridinium N-oxide

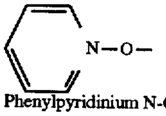

Phenylpyridinium N-Oxide

Carboxylic Acids from Mixed Anhydride Leaving Groups

Carboxylic acid leaving groups have the structure

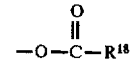

wherein $R^{18}$ is $C_{1-10}$ alkyl, preferably $C_{1-4}$ alkyl, most preferably either $CH_3$ or $CH_2CH_3$ and mixtures thereof.

When $R^{18}$ is $C_1$ and above, it is believed that the leaving groups will form carboxylic acids upon perhydrolytic conditions. Thus, when $R^{18}$ is $CH_3$, acetic acid would be the leaving group; when $CH_2CH_3$, propionic acid would the leaving group, and so on. However, this is a possible explanation for what may be a very complicated reaction.

Examples of mixed anhydride esters include alkanoyloxyacetyl-oxyacetic or alkanoyl-oly[oxyacetyl]oxyacetic/acetic or propionic mixed anhydride.

Delivery Systems

The precursors can be incorporated into a liquid or solid matrix for use in liquid or solid detergent bleaches by dissolving into an appropriate solvent or surfactant or by dispersing onto a substrate material, such as an inert salt (e.g., NaCl, $Na_2SO_4$) or other solid substrate, such as zeolites, sodium borate, or molecular sieves. Examples of appropriate solvents include acetone, non-nucleophilic alcohols, ethers or hydrocarbons. Other more water-dispersible or -miscible solvents may be considered. As an example of affixation to a substrate material, the precursors of the present invention could be incorporated onto a non-particulate substrate such as disclosed in published European patent application EP No. 98 129.

While substituting solubilizing groups may improve the solubility and enhance the reactivity of these precursors, an alternate mode and preferred embodiment is to combine the precursors with a surfactant.

For example, the inventive precursors with oxynitrogen leaving groups are apparently not as soluble in aqueous media as compared to phenyl sulfonates. Other precursors may be similarly somewhat less soluble than phenyl sulfonate esters. Thus, a preferred embodiment of the invention is to combine the precursors with a surfactant to form granules. It is particularly preferred to coat these precursors with a nonionic or anionic surfactant that is solid at room temperature and melts at above about 40° C. A melt of surfactant may be simply admixed with peracid precursor, cooled and chopped into granules. Exemplary surfactants for such use are illustrated in Table 1 below.

TABLE 1

| Commercial Name | m.p. | Type | Supplier |
|---|---|---|---|
| Pluronic F-98 | 55° C. | Nonionic | BASF Wyandotte |
| Neodol 25-30 | 47° C. | Nonionic | Shell Chemical |
| Neodol 25-60 | 53° C. | Nonionic | Shell Chemical |
| Tergitol-S-30 | 41° C. | Nonionic | Union Carbide |
| Tergitol-S-40 | 45° C. | Nonionic | Union Carbide |
| Pluronic 10R8 | 46° C. | Nonionic | BASF Wyandotte |
| Pluronic 17R8 | 53° C. | Nonionic | BASF Wyandotte |
| Tetronic 90R8 | 47° C. | Nonionic | BASF Wyandotte |
| Amidox C5 | 55° C. | Nonionic | Stepan |

The precursors, whether coated with the surfactants or not so coated, could also be admixed with other surfactants to provide either bleach additive or detergent compositions.

Particularly effective surfactants appear to be non-ionic surfactants. Preferred surfactants include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides and their ethoxylated derivatives.

Anionic surfactants may also be suitable. Examples of such anionic surfactants may include the ammonium, substituted ammonium (e.g., mono-, di-, and triethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, alpha olefin sulfonates, hydroxyalkane sulfonates, fatty acid monoglyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Suitable amphoteric and zwitterionic surfactants containing an anionic water-solubilizing group, a cationic group or a hydrophobic organic group include amino carboxylic acids and their salts, amino dicarboxylic acids and their salts, alkyl-betaines, alkyl aminopropylbetaines, sulfobetaines, alkyl imidazolinium derivatives, certain quaternary ammonium compounds, certain quaternary phosphonium compounds and certain tertiary sulfonium compounds.

As mentioned above, other common detergent adjuncts may be added if a bleach or detergent bleach product is desired. If, for example, a dry bleach composition is desired, the following ranges (weight %) appear practicable:

| | |
|---|---|
| 0.5–50.0% | Hydrogen Peroxide Source |
| 0.05–25.0% | Precursor |
| 1.0–50.0% | Surfactant |
| 1.0–50.0% | Buffer |
| 5.0–99.9% | Filler, stabilizers, dyes, Fragrances, brighteners, etc. |

The hydrogen peroxide source may be selected from the alkali metal salts of percarbonate, perborate, persilicate and hydrogen peroxide adducts and hydrogen peroxide. Most preferred are sodium percarbonate, sodium perborate mono- and tetrahydrate, and hydrogen peroxide. Other peroxygen sources may be possible, such as monopersulfates and monoperphosphates. In liquid applications, liquid hydrogen peroxide solutions are preferred, but the precursor may need to be kept separate therefrom prior to combination in aqueous solution to prevent premature decomposition.

The range of peroxide to peracid precursor is preferably determined as a molar ratio of peroxide to precursor. Thus, the range of peroxide to each precursor is a molar ratio of from about 0.1:1 to 10:1, more preferably about 1:1 to 10:1 and most preferably about 2:1 to 8:1. This peracid precursor/peroxide composition should provide about 0.5 to 100 ppm A.O., more preferably about 1 to 50 ppm peracid A.O. (active oxygen), and most preferably about 1 to 20 ppm peracid A.O., in aqueous media.

An example of a practical execution of a liquid delivery system is to dispense separately metered amounts of the precursor (in some non-reactive fluid medium) and liquid hydrogen peroxide in a container such as described in Beacham et al., U.S. Pat. No. 4,585,150, issued Apr. 29, 1986.

The buffer may be selected from sodium carbonate, sodium bicarbonate, sodium borate, sodium silicate, phosphoric acid salts, and other alkali metal/alkaline earth metal salts known to those skilled in the art. Organic buffers, such as succinates, maleates and acetates may also be suitable for use. It appears preferable to have sufficient buffer to attain an alkaline pH. It is especially advantageous to have an amount of buffer sufficient to maintain a pH in the range of about 8.5 to about 10.5.

The filler material (which may actually constitute the major constituent by weight of the detergent bleach) is usually sodium sulfate. Sodium chloride is another potential filler. Dyes include anthraquinone and similar blue dyes. Pigments, such as ultramarine blue (UMB), may also be used, and can have a bluing effect by depositing on fabrics washed with a detergent bleach containing UMB. Monastral colorants are also possible for inclusion. Brighteners, such as stilbene, styrene and styrylnaphthalene brighteners (fluorescent whitening agents), may be included. Fragrances used for aesthetic purposes are commercially available from Norda, International Flavors and Fragrances and Givaudon. Stabilizers include hydrated salts, such as magnesium sulfate, and boric acid.

Experimental aspects of the invention will be illustrated with a particularly preferred peracid activator referred to in abbreviated form as "EACPS," the detailed preparation of which is illustrated by Example 1. The inventive embodiments may be viewed as having the structure illustrated by Formula 2:

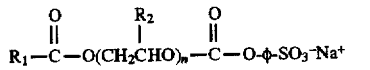

FORMULA 2 where $R_1$ is alkyl or branched alkyl of 1–16 carbons and $R_2$ is H or methyl. The EACPS embodiment is where $R_1$ is $C_8H_{15}$ and $R_2$ is H.

Briefly, the particular EACPS embodiment was prepared from octanoyl chloride and ethylene glycol as starting materials and the first synthesis step of the Formula 2 compound was carried out in ethyl acetate in the presence of pyridine. The resulting hydroxyethyl ester was isolated by distillation and then reacted with phosgene to form the chloroformate. The chloroformate in turn was reacted with monosodium phenol sulfonate in the presence of pyridine to form the sodium salt of the product. This was isolated by conversion to the free acid and extraction into ethyl acetate. The ethyl acetate was removed, the free acid was dissolved in methanol, and was converted to the sodium salt with sodium carbonate. Ethylene oxide could be used as starting material instead of ethylene glycol.

The EACPS compound was tested for peracid yield as a percentage of theoretical maximum, and was found to provide 87% yield within two minutes at 20° C. solution and in 35° C. solution. At six minutes, the inventive precursor provided 87% yield at 20° C. solution and 77% at 35° C. solution. After 12 minutes, the inventive precursor provided 86% yield in 20° C. solution and 67% in 35° C. solution. Thus, the inventive precursor gave excellent peracid yields within 12 minutes, which is a typical wash cycle and at temperatures illustrating room temperature and hot water washing.

The particularly preferred embodiment gave excellent stain removal performance results, as summarized by Table 2, below.

TABLE 2

| | 8-Stain Stain Average[2] | | Clay/ 3-Fabric Average[3] | |
|---|---|---|---|---|
| Control: | 20° C. | 35° C. | 20° C. | 35° C. |
| Base[1] + 20 ppm $H_2O_2$ | 68.2 | 77.5 | 76.7 | 84.7 |
| Base[1] + 40 ppm $H_2O_2$ | 67.7 | 78.9 | 78.3 | 83.6 |
| Base[1] + 20 ppm $H_2O_2$ + 3 ppm theoretical A.O. from EACPS | 69.1 | 79.9 | 82.7 | 90.0 |
| Base[1] + 40 ppm $H_2O_2$ + 3 ppm theoretical A.O. from EACPS | 70.7 | 81.4 | 84.3 | 90.7 |
| LSD, 95% t-test | 0.9 | 0.8 | 1.4 | 1.3 |

[1]Base detergent is nonionic, phosphate formula.
[2]8-stain average = grass, gravy, spaghetti, tea, coffee, grape, berry, mustard.
[3]Clay/3-fabric average = bandy-black clay on cotton, polycotton, polyester.

The EACPS embodiment provides optimum available oxygen yield at about pH 10.5 (with 80% of theoretical A.O. yield in the presence of a non-phosphate, anionic detergent at 12 minutes, pH 10.5). An optimal perborate to precursor ratio with the EACPS embodiment is believed to be in the range of about 4:1 to about 3:1, although a 2:1 ratio provides good results also.

Table 3 lists the A.O. profile produced by EACPS as a function of temperature, which data was obtained from washing machine experiments. The data is given as peracid yield as a percentage of theoretical maximum.

TABLE 3

| | 2 Minutes | | 6 Minutes | | 12 Minutes | |
|---|---|---|---|---|---|---|
| | 20° C. | 35° C. | 20° C. | 35° C. | 20° C. | 35° C. |
| EACPS inventive embodiment | 87% | 87% | 87% | 77% | 86% | 67% |

EXAMPLE 1

Pyridine (120 g, 1.5 mol) was mixed with 200 g ethylene glycol and 600 ml of ethyl acetate. Next, octanoyl chloride (1 mol) was added dropwise, over a period of 2 hours. A steady exotherm ensued, and the reaction mixture reached 45°. The reaction was stirred until it cooled spontaneously.

Water (500 ml) was added and the mixture was concentrated on vacuo, to the point where all of the ethyl acetate was evaporated. Heptane (500 ml) was added, the mixture shaken, and the water/glycol layer was discarded. The heptane layer was washed with 1×500 ml of 20% $H_3PO_4$ and 1×500 ml $H_2O$. The heptane layer was concentrated, and the residue distilled under high vacuum. The material so synthesized was 2-(hydroxyethyl) octanoate.

bp 95°–100°/0.1 torr

Yield=150 g, or 80%.

The above-prepared 2-(hydroxyethyl) octanoate (47 g, 0.25 mol) was dissolved in 400 ml heptane, cooled under argon to −78° and treated with 130 ml of 2.2 molar $COCl_2$/$CHCl_3$. Next, 21 g (0.26 mol) of pyridine was added. A thick white precipitate formed. The mixture was stirred, warmed to room temperature over 3 hours, filtered, and concentrated in vacuo. The resulting oil was mixed with 42 g anhydrous sodium 4-hydroxylbenzenesulfonate (0.214 mol) and 300 ml $CH_3CN$, and cooled to 0° under argon. Pyridine (21 g, 0.26 mol) was added; the ice-bath was removed and the mixture stirred for 3 hours. A precipitate of 12 g of reaction product was collected, and the reaction was worked up to isolate the rest of the reaction product.

The $CH_3CN$ was evaporated in vacuo, and 700 mL ethyl acetate was added. Next, the ethyl acetate solution was extracted with 1×250 ml ice-cold 10% $H_2SO_4$. The ethyl acetate layer was then dried with $MgSO_4$, filtered, and concentrated in vacuo. The residue was dissolved in 400 ml of methanol and 17.6 g (0.21 mol) of $NaHCO_3$ was added, and the mixture was stirred for 1 hour, at which time, $CO_2$ evolution ceased. The mixture was concentrated to 150 ml in vacuo, and the reaction product, which had partially precipitated, was driven completely out of solution by addition of 400 ml of ethyl acetate, and collected by filtration. Yield=43 g of EACPS.

The thus described reaction product, which is an embodiment of the invention (sodium 4-(2-octanoyloxy ethoxy carbonyloxy) benezensulfonate) was recovered in total yield (including the 12 g which precipitated prior to workup) as 55 g, or 50%.

Embodiments of the invention represent a new series of activators that can be singularly ethoxylated or proproxylated due to the relative $pK_a$'s of the acid and alkoxide functionalities and the reactivity of ethylene and propylene oxide. Embodiments of the invention show improved A.O. stability at elevated temperatures, and the inventive activators produce statistically significant performance improvements on a variety of stains and bandy-black clay at several different temperatures. The clay performance is especially significant because bandy-black clay results correlate well with "dingy-soil" cleaning on consumer garments. In preparing activators of this invention, higher molecular weight polyethylene or propylene glycols can readily be used while polyethoxylating or propoxylating.

It is to be understood that while the invention has been described above in conjunction with preferred specific embodiments, the description and examples are intended to illustrate and not limit the scope of the invention, which is defined by the scope of the appended claims.

It is claimed:

1. A bleaching composition comprising:

(a) a peracid activator having the structure

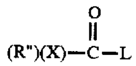

where R" is R'

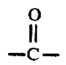

and R' is $C_{4-12}$ alkyl or alkoxylated alkyl, where X is a polyhydroxy derivative of the structure $—O[CH_2CH_2O]_n$ or $—O[CH_2CHCH_3O]_n$ and n is 1 to about 7, and where L is a leaving group selected from the group consisting of:

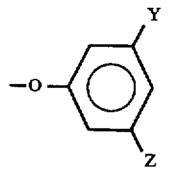

(i)

wherein Y and Z are individually H, $SO_3M$, $CO_2M$, $SO_4M$, OH, halo substituent, $OR^2$, $R^3$, $NR_3{}^4X$, and mixtures thereof, wherein M is an alkali metal or alkaline earth metal counterion, $R^2$ is $C_{1-20}$ alkyl, $R^3$ is $C_{1-6}$ alkyl, $R^4$ is $C_{1-30}$ alkyl and X is a counterpart ion thereto, and Y and Z can be the same or different;

(ii) halide;

(iii) $—ONR^6$, wherein $R^6$ contains at least one carbon which is singly or doubly bonded directly to N;

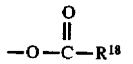

(iv)

wherein $R^{18}$ is $C_{1-10}$ alkyl; and (v) mixtures thereof; and (b) a bleach-effective amount of a peroxygen source.

2. The bleaching composition of claim 1 wherein the leaving group is —O—Ø—$SO_3M$.

3. The bleaching composition as in claim 1 wherein the activator has the structure

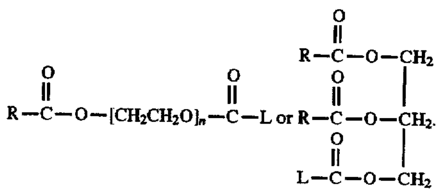

4. A peracid activator having the structure
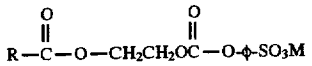
wherein R is a $C_{4-12}$ linear or branched alkyl and M is an alkali metal or alkaline earth metal counterion.
5. The activator as in claim 4 where R is $—C_7H_{15}$.
* * * * *

UNITED STATES PATENT AND TRADEMARK OFFICE

CERTIFICATE OF CORRECTION

PATENT NO. : 5,705,091

DATED : January 6, 1998

INVENTOR(S) : Dale S. Steichen et al.

It is certified that error appears in the above-identified patent and that said Letters Patent is hereby corrected as shown below:

In Column 8 at Line 54 replace:

"cycle of 5 carbon atoms and can be alkyl or aryl substituted." with

--cycle of 5 carbon atoms and can be $C_{1-6}$ alkyl or aryl substituted.--

In Column 9 at Line 29 replace:

"leaving group; when $CH_2CH_3$, propionic acid would the" with

--leaving group; when $CH_2CH_3$, propionic acid would be the--

In Column 13 at Line 48 replace:

"evolution ceased. The mixture was concentrated to 150 ml in" with

--evolution ceased. The mixture was concentrated to '150 ml in--

Signed and Sealed this

Twenty-first Day of April, 1998

Attest:

BRUCE LEHMAN

Attesting Officer

*Commissioner of Patents and Trademarks*